(12) United States Patent
Kaufman

(10) Patent No.: US 10,006,871 B2
(45) Date of Patent: Jun. 26, 2018

(54) METHODS AND APPARATUS FOR DETECTING AIRBORNE MOLECULAR CONTAMINANTS

(75) Inventor: Stanley L. Kaufman, New Brighton, MN (US)

(73) Assignee: TSI, Incorporated, Shoreview, MN (US)

( * ) Notice: Subject to any disclaimer, the term of this patent is extended or adjusted under 35 U.S.C. 154(b) by 936 days.

(21) Appl. No.: 13/238,196

(22) Filed: Sep. 21, 2011

(65) Prior Publication Data

US 2012/0241601 A1   Sep. 27, 2012

Related U.S. Application Data

(60) Provisional application No. 61/393,962, filed on Oct. 18, 2010, provisional application No. 61/393,965, filed on Oct. 18, 2010.

(51) Int. Cl.
*G01N 21/94* (2006.01)
*G01N 21/45* (2006.01)
*G01N 15/06* (2006.01)

(52) U.S. Cl.
CPC ......... *G01N 21/94* (2013.01); *G01N 15/0612* (2013.01); *G01N 21/45* (2013.01); *G01N 15/065* (2013.01); *G01N 2021/458* (2013.01)

(58) Field of Classification Search
CPC ............. G01N 21/94; G01N 2021/945; G01N 21/9501; G01N 21/9018; G01N 2021/752; G01N 1/2273; G01N 23/225
(Continued)

(56) References Cited

U.S. PATENT DOCUMENTS 6,018,391 A * 1/2000 Yoshida ................. 356/484
6,943,893 B2 * 9/2005 Chou et al. ............ 356/484
(Continued)

OTHER PUBLICATIONS

Bruel, Laurent. "Environmental effects on optical component aging." XXXIV Annual Symposium on Optical Materials for High Power Lasers: Boulder Damage Symposium. International Society for Optics and Photonics, 2003.*
(Continued)

*Primary Examiner* — Tri Ton
*Assistant Examiner* — Rebecca C Bryant
(74) *Attorney, Agent, or Firm* — Patterson Thuente Pedersen, P.A.

(57) ABSTRACT

Methods and apparatuses for the removal, analysis and/or detection of harmful airborne molecular contaminants (AMCs). In one embodiment, an ionizing radiation source is utilized to remove the harmful AMCs from a flow stream via radiolytic particle generation and subsequent capture by filtration. The captured particles may be released, for example, by re-gasification for analysis at much higher concentrations. In another embodiment, the ionizing radiation source is utilized with a particle detector to sense when harmful AMCs are present. In one embodiment, a solid optical medium is exposed to a monitored environment so that the AMCs are in contact with a surface of the solid optical medium. A focused light beam is arranged to emerge from a solid optical medium at an energy density sufficient to cause the AMCs to form deposits on the exposed surface of the solid optical medium, which can be detected using an interferometric technique.

10 Claims, 3 Drawing Sheets

(58) Field of Classification Search
USPC .......................... 356/237.3–237.5, 450–471
See application file for complete search history.

(56) References Cited

U.S. PATENT DOCUMENTS

| | | | |
|---|---|---|---|
| 7,295,302 B2* | 11/2007 | Magniez | 356/237.3 |
| 2005/0057756 A1* | 3/2005 | Fang-Yen et al. | 356/497 |
| 2011/0149294 A1* | 6/2011 | Song | 356/477 |
| 2013/0119242 A1* | 5/2013 | Goddard et al. | 250/227.14 |

OTHER PUBLICATIONS

Madelaine et al., "Formation and evolution of ultrafine particles produced by radiolysis and photolysis," J. Geophys. Res. (1988), vol. 85, issue C12, pp. 7471-7474.

Billard et al., "Evolution of condensation nuclei formed by radiolysis of gaseous impurities of air," Compt. Rendus, Ser. A & B, vol. 265, pp. 1376-1379 (Dec. 18, 1967) (including Machine translation (4 pages).

* cited by examiner

METHODS AND APPARATUS FOR DETECTING AIRBORNE MOLECULAR CONTAMINANTS

RELATED APPLICATIONS

This application claims the benefit of U.S. Provisional Application No. 61/393,962, filed Oct. 18, 2010, and of U.S. Provisional Application No. 61/393,965, filed Oct. 18, 2010, the disclosures of which are hereby incorporated by reference in their entirety.

BACKGROUND

"Airborne molecular contaminants" or AMCs, is a term of art in the area of clean room operation, referring to gaseous contaminants. Certain gaseous contaminants cause problems due to deposition or formation of particles or haze matter on sensitive surfaces involved in a photolithography process during processing. Such surfaces include semiconductor wafers, lenses, mirrors, beam splitters, photomasks, semiconductor wafers, and pellicle films. While the detailed processes leading to particle formation is the subject of ongoing research, it is clear that they originate from gases because they cannot be eliminated by particle filtering.

A consequence of AMCs is the formation of "ultraviolet haze" on surfaces in lithography processes. Ultraviolet haze is attributed to the presence of airborne molecular contaminants which react in the presence of the ultraviolet light used in lithography to form the haze. A sensor is required to detect the presence of these contaminants and thus avoid exposing the high-value semiconductor products.

The contaminant concentration can be so low, e.g. parts per trillion, that it becomes difficult to use almost any analytical technique to investigate the contaminant composition and thus trace its origin. Existing work in the area of particle contamination produced by AMCs uses sophisticated and expensive analytical methods such as gas chromatography (GC), TOF-SIMS, and other methods to identify gaseous chemical species present regardless of whether these species cause particle deposition. These methods suffer from lack of knowledge of what contaminants will form the deposits. Attempts to discover which species are correlated with the particle formation ensue. Ultimately this could lead to understanding the chemical reactions and pathways leading to particle deposition, but it is a long and difficult process.

Another known method is to use mechanical oscillators such as piezoelectric and surface acoustic wave devices to sense the deposits by sensing their mass. This method correctly targets even unknown contaminants capable of forming the haze, but suffers from insufficient sensitivity due to mass detection limits.

Aside from detection of AMCs, removal of harmful AMCs also poses significant challenges. Gas filters and absorbers can be utilized in principle, but it is very difficult to reach the parts-per-trillion purity levels needed to prevent haze formation. A new clean room, for example, typically requires a run-in time of several weeks, during which the AMC level as indicated by haze formation gradually decreases as the sources of AMCs outgas. Therefore, elimination of AMCs that cause haze poses a significant problem. Another technique is to distill the AMCs out of the air, which is a costly process.

Methods and/or apparatuses for detection and elimination of particles formed from AMCs that are more efficient and cost effective would be welcome. Efficient and cost-effective methods and apparatuses for detection of particles formed from AMCs would also be a welcome capability.

SUMMARY OF THE INVENTION

Various embodiments of the invention include methods and apparatuses for detecting the presence of AMCs. In one embodiment of the invention, a light beam emerging from a solid optical medium causes the formation of deposits formed from the AMCs on the surface of the solid which disturb the wavefront of the light beam. Subtle changes in the wavefronts can be detected, for example by interferometry. The deposits are formed from contaminants in the atmosphere surrounding the focused spot, but they will only form if those contaminants are capable of the specific type of reaction needed to produce the deposits. The contaminants which form the deposits are the kinds of contaminants which produce ultraviolet haze in mask operations in semiconductor clean rooms. Accordingly, this mechanism can be used to monitor for the presence of the contaminants.

Highly sensitive detection of these changes can be made for example by interferometry, in which the phase of a probe beam tightly focused at the solid surface is compared with that of a reference beam passing through a reference solid surface with power density at the reference surface much lower than that of the probe beam focused at its solid surface. The rate of formation of deposits increases as a strongly nonlinear function of the power density, i.e., $I^N$ where N>1. The growth of the deposit causes a difference in the phases of the two beams of the interferometer.

A less sensitive but less costly method to detect the deposit would be by observing the growth of a ring pattern indicative of spherical aberration in the beam focused at the surface, due to the lens like effect of the deposit which becomes thickest in the center of the beam and tapers off at the edges. With this less sensitive method, no reference beam is required. The deposits are formed from contaminants in the atmosphere surrounding the focused spot, but they will only form if those contaminants are capable of the specific type of reaction needed to produce the deposits.

Still other embodiments of the invention operate on the phenomenon of radiolytic particle formation as a way to both selectively detect and to remove AMCs that are capable of forming particles. Hereinafter, AMCs that are capable of forming particles are referred to as "harmful AMCs." In one embodiment, particles that are formed radiolytically are captured and optionally re-gasified for analysis. The flow stream is conditioned by the condensing of the particles radiolytically, which removes the harmful AMCs from the flow stream. The re-gasification can selectively increase the concentration of the contaminants that are capable of forming ultraviolet haze films for enhanced analytical sensitivity.

Compared with the current methods, the various embodiments of the invention are more practical than current methods and apparatuses for identifying contaminants because they identify only species that are of interest. There is no response to gases that are non-particle-forming. Inactive species do not interfere with the measurement and method. Various embodiments of the present invention are substantially lower in cost than existing methods and apparatuses for contaminant detection and removal.

Radiolytic formation of particles is a source of particle background when using various types of aerosol neutralizers that utilize ionizing radiation sources. Generally, the amount of particles formed by this mechanism depends on the amount of AMC present, the strength of the ionizing radiation and the dwell time of the gas in the irradiated zone.

Copious particle production has been observed using commercially-available Po-210 ionizers, and also with soft x-ray sources. Even a few millicuries of Krypton-85, a much weaker ionization source than Po-210 or soft x-ray sources, will affect particle formation for dwell times on the order of minutes. Any source of alpha, beta, gamma, X, or ultraviolet radiation can potentially produce particles by this mechanism. Published literature on radiolytic particle formation dates back several decades to at least to the 1960's. See, e.g., Billard et al., "Evolution of condensation nuclei formed by radiolysis of gaseous impurities of air," Compt. Rendus, Ser. A and B, vol. 265, pp. 1376-1379 (18 Dec. 1967), and Madelaine et al., "Formation and evolution of ultrafine particles produced by radiolysis and photolysis," J. Geophys. Res. (1980) Vol. 85, issue C12, pp. 7471-7474, the disclosures of which are hereby incorporated by reference except for express definitions contained therein.

Radiolytic formation of particles has been regarded mainly as a nuisance in aerosol science, due to the non-discriminate production of particles of unknown composition that interfere with the particles to be measured. Certain embodiments of the invention utilize these characteristics of radiolytic particle production to provide the advantage of sensing when AMCs may form harmful particles having harmful consequences such as ultraviolet haze.

Structurally, various embodiments of the invention utilize a substantially monochromatic light source such as an actinic-wavelength laser light that emerges from an optical fiber, or is focused on a clean substrate. The high density actinic-wavelength light at the surface of the fiber or substrate can cause the formation of deposits on the surface of the fiber or substrate when in the presence of AMCs. Such phenomena can sometimes be observed with the transmission of laser light through single-mode optical fibers, causing a so-called "polymer bump" to grow on the end of the fiber. The deposits disturb the laser beam wavefront. The distortion of the emerging wavefront ultimately leads to a change in the beam intensity profile from a smooth Gaussian shape to one with rings and other irregularities. Prior to these gross effects, far more subtle changes in the wavefronts can be detected, for example by interferometry. Hence, enhanced sensitivity may be provided by using an interferometer to detect wave-front shape changes or phase changes.

In one embodiment of the invention, a method for detecting the presence of airborne molecular contaminants includes producing a primary beam of electromagnetic radiation that propagates at a substantially monochromatic wavelength. The primary beam of electromagnetic radiation is split into a first beam and a second beam. The first beam is propagated through a solid medium that is transmissive at the substantially monochromatic wavelength, the first beam exiting the solid medium at a first surface. The first surface of the solid medium is exposed to an environment containing the airborne molecular contaminants, the first beam of electromagnetic radiation causing the airborne molecular contaminants to form deposits on the first surface of the solid medium. The method then involves measuring a phase shift between the first beam exiting the first surface and the second beam, the phase shift being caused by the deposits formed on the first surface.

In other embodiments of the invention, radiolytic formation of particles condenses the contaminant material in the form of nanometer-scale particles, which are then accumulated by filtration. The accumulated material is not only removed from the flow stream (thus conditioning the flow stream) but can then be released into a small gas or liquid volume, thus effecting a high degree of concentration and increasing the sensitivity of any analytical technique used to investigate the contaminant material and origin. By allowing the contaminant to form particles under ionizing radiation, and capturing these particles on a filter, only materials that are problematic are accumulated, regardless of their composition.

In one embodiment of the invention, a method for detecting airborne molecular contaminants includes:
  providing a treatment chamber comprising an inlet filter, an ionizing radiation source and particle detector, the inlet filter being a high efficiency filter;
  filtering a gas stream with the inlet filter so that the gas stream is substantially free of particles when the gas stream enters the treatment chamber;
  causing the gas stream to flow through the treatment chamber, the gas stream including trace gas constituents that constitute airborne molecular contaminants;
  irradiating the gas stream with an ionizing radiation from the ionizing radiation source as the gas stream passes through the treatment chamber, the irradiating causing radiolytic formation of particles in the gas stream; and
  detecting the particles that are formed from the irradiating with the particle detector.

In another embodiment of the invention, a method for removing and identifying the materials of airborne molecular contaminants includes:
  providing a treatment chamber comprising an ionizing radiation source, the treatment chamber being in fluid communication with an inlet filter and an exit filter, the inlet and exit filters being high efficiency filters;
  passing a gas stream through the inlet filter and into the treatment chamber, the inlet filter filtering the gas stream so that the gas stream is substantially free of particles when the gas stream enters the treatment chamber, the gas stream entering the treatment chamber with a gas constituent that causes airborne molecular contaminants;
  irradiating the gas stream with an ionizing radiation from the ionizing radiation source as the gas stream passes through the treatment chamber, the irradiating causing radiolytic particles to form in the gas stream;
  capturing with the exit filter the radiolytic particles that are formed from the irradiating; and
  causing the gas stream to exit the exit filter into a treated environment.

To identify the materials of the AMCs, the method may further include:
  providing means for selectively isolating the treatment chamber from fluid communication with the exit filter;
  providing a heat source for heating the exit filter, the exit filter being adapted to be selectively placed in fluid communication with a gas analyzer;
  isolating the exit filter from the treatment chamber after capturing the radiolytic particles with the exit filter;
  placing the exit filter in fluid communication with the gas analyzer when the exit filter is isolated from the treatment chamber;
  heating the exit filter with the heat source after capturing the radiolytic particles with the exit filter and when the gas analyzer is in fluid communication with the gas analyzer, the heating causing the radiolytic particles to gasify for analysis with the gas analyzer.

DETAILED DESCRIPTION

Figure 1:
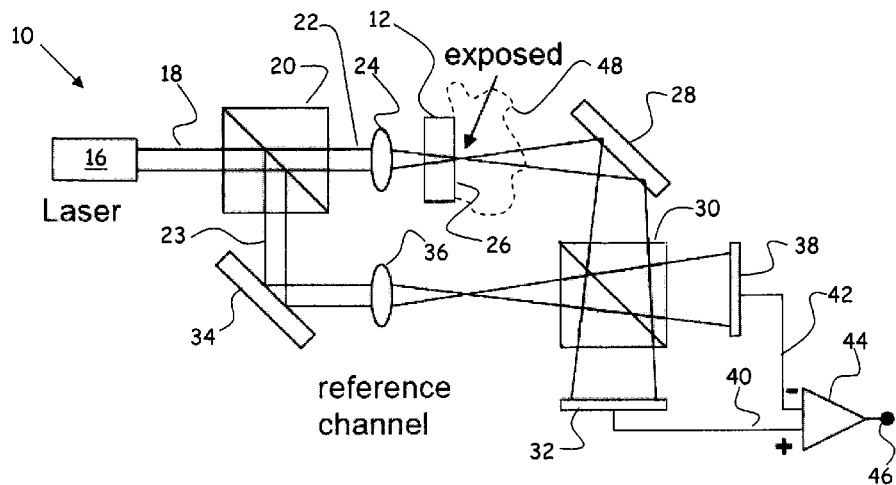
FIG. 1 is a schematic of an interferometer for detecting the formation of deposits on a substrate in an embodiment of the invention.
Figure 2:
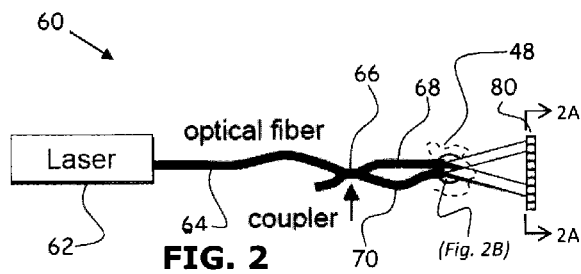
FIG. 2 is a schematic of a fiber optic-based interferometer for detecting the formation of deposits on a fiber optic in an embodiment of the invention.
Figure 2A:
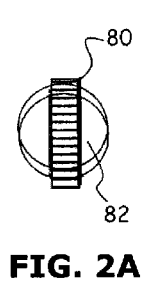
FIG. 2A is a schematic of overlapping laser light that causes an interference pattern on an array detector of FIG. 2.
Figure 2B:
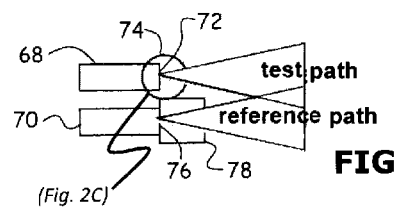
FIG. 2B is a close up schematic of a test arm and a reference arm fiber optic of FIG. 2.
Figure 2C:
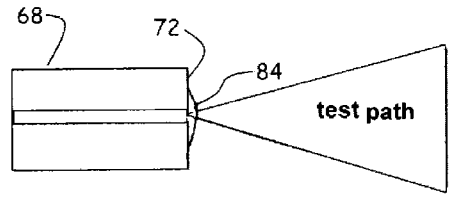
FIG. 2C is a close up of a deposit on the test arm fiber optic of FIGS. 2 and 2B.

Referring to FIG. 1, a Mach-Zender type interferometric system 10 including a substrate element 12 for gathering deposits from airborne molecular contaminants (AMCs) is depicted in an embodiment of the invention. The interferometric system 10 includes an electromagnetic source 16 (in this case a laser) that propagates a primary beam 18 of electromagnetic radiation at a substantially monochromatic wavelength. In this embodiment, the primary beam 18 is routed through a beam splitter 20 that splits the primary beam 18 into a test beam 22 and a reference beam 23. The test beam 22 is routed through a set of optical components comprising a focusing optic 24 and the substrate element 12, the focusing optic 24 focusing the test beam 22 at a measuring surface 26 of the substrate element 12. The test beam 22 can be routed via a redirecting optic 28 through a second beam splitter 30 before being subtended by a test beam detector 32.

Likewise, the reference beam 23 can be routed through a set of optical components comprising a redirecting optic 34, a focusing optic 36 and a second beam splitter 30, which direct the test beam onto a reference beam detector 38. The respective optical components that propagate the test and reference beams each define an optical path having an optical path length.

In one embodiment, the test and reference detectors 32 and 38 are adapted to output test and reference signals 40 and 42, respectively, to an amplifier 44 that subtracts the reference signal 42 from the test signal 40 to produce an output signal 46.

The wavelength may be of a suitable monochromatic wavelength such as green, blue or ultraviolet. The substrate element 12 should have a high transmissivity at the monochromatic wavelength, and thus may be fabricated from a material such as glass or silica. Herein, a beam of light is "substantially monochromatic" if the spectral profile is adequate for purposes of interferometry. Lasers typically emit electromagnetic radiation having a substantially monochromatic spectral profile, i.e., a dominant central wavelength with a very narrow width at half the local maximum emission. Substantially monochromatic light may also be found in non-laser sources (e.g., mercury lamps), as well as with continuous emitters that are filtered so that only a narrow band pass is propagated.

In operation, the measuring surface 26 is exposed to an atmosphere 48 to be monitored. The energy density of the focused test beam 22 at the measuring surface 26 causes the AMCs in the atmosphere 48 to form deposits on the measuring surface 26. The test beam 22 emerging from the focus is measured interferometrically in reference to the reference beam 23 to detect changes in the phase. The phase change is caused by the deposit or collection of contaminants on the measuring surface 26 that alters the test optical path length. The rate of phase change is proportional to the concentration of the contaminants present in the atmosphere 48. In the depicted embodiment, the phase shift causes an increase in the power of the reference beam 23 reaching the reference beam detector 38 while decreasing the power of the test beam 22 reaching the test beam detector 32.

Referring to FIGS. 2 and 2A-2C, a fiber optic-based system 60 for detecting deposits from airborne molecular contaminants (AMCs) is depicted in an embodiment of the invention. The fiber optic-based system 60 includes a laser light source 62 operatively coupled to an optical fiber 64. The optical fiber 64 is routed through a coupler 66 which divides the laser light between a test fiber optic 68 and a reference fiber optic 70. Here, the test optical path comprises the test fiber optic 68 and the reference optical path comprises the reference fiber optic. A distal end 72 of the test fiber optic 68 is left exposed to an atmosphere 74 to be monitored while a distal end 76 of the reference fiber optic 70 is protected with a transmissive shroud 78 such as a piece of glass. The laser light exiting the test fiber optic 68 and the reference fiber optic 70 are directed to overlap each other, the overlap region being subtended at least in part by an array detector 80. The array detector 80 is of sufficient spatial resolution to detect an interference pattern 82 created by the overlapping laser light exiting the test fiber optic 68 and the reference fiber optic 70.

In operation, the energy density of the laser light exiting the test fiber optic 68 causes the AMCs in the atmosphere 74 to form a deposit 84 on the distal end 72 of the test fiber optic 68. (Deposits are not formed on the transmissive shroud 78 because the exposed surface of the transmissive shroud 78 is substantially removed from the high density point of the reference fiber optic.) The deposits 84 that collect on the test fiber optic 68 cause a change in the optical path length of the test optical path length, resulting phase shift in the laser light exiting the distal end 72 of the test fiber optic 68 relative to the laser light exiting the reference fiber optic 70. The phase shift causes the interference pattern 82 to shift. The array detector 80 senses the shift in the interference pattern 82. The rate of shifting of the interference pattern 82 is proportional to the amount of harmful AMCs in the atmosphere 74.

The reference beam can be isolated the contaminant to preclude growth of deposits on surfaces through which the reference beam passes. Even if reference surfaces are exposed, the intensity of the reference beam at these surfaces can be reduced by using an unfocused or collimated reference beam in contrast to the focused probe beam. For example if the beam diameter is 10 mm for the reference beam and 100 micrometers (0.1 mm) at the test surface (e.g., at the measuring surface 26 or the distal end 72 of the test fiber optic 68), the ratio of the test beam intensity to the reference beam intensity is on the order of $(10 \text{ mm}/0.1 \text{ mm})^2$ or 10,000. If the deposits form at a non-linear rate proportional to $I^N$ where $N>1$, then the ratio of the growth of the focused beam to the unfocused beam is further enhanced. For example, for the 10,000 ratio above and for AMCs that form deposits at a rate proportional to the square of the intensity (i.e., N=2), the growth rate will be on the order of 100 million times greater on the test surface than in the reference beam.

Figure 3:
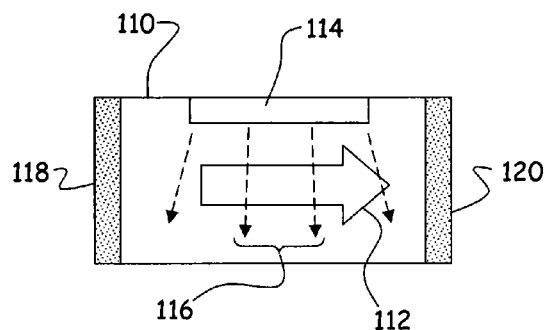
FIG. 3 is a schematic of a conditioning chamber for removing harmful AMCs from a flow stream in an embodiment of the invention.

Referring to FIG. 3, a conditioning chamber 110 for removing harmful AMCs from a flow stream 112 is depicted in an embodiment of the invention. The conditioning chamber 110 includes an ionizing radiation source 114 arranged to bombard the flow stream 112 with ionizing radiation 116. Optionally, an inlet filter 118 may be arranged to filter the flow stream 112 as it enters the conditioning chamber 110. An exit filter 120 can be arranged to filter the flow stream 112 as it exits the conditioning chamber 110.

In operation, the inlet filter 116 removes ambient particles from the flow stream 112 as it enters the conditioning chamber 110. The ionizing radiation causes particles to be radiolytically formed from the harmful AMCs present in the flow stream 112. The exit filter 120 captures the particles that were radiolytically formed by the ionizing radiation 116. The exit filter 120 may be subsequently removed and analyzed to determine the composition of the AMCs that caused the radiolytic particle formation.

The ionizing radiation source 114 may be any of several radiation sources available to the artisan, including but not limited to Po-210 ionizers, Krypton-85 and soft x-ray sources. The strength of the ionizing radiation source 114, in combination with parameters that affect the dwell time of the flow stream 112 within the conditioning chamber 110 (e.g., flow rate, chamber size) can be tailored so that essentially all harmful AMCs are condensed out of the flow stream 112 by the radiolytic process.

In one embodiment, the inlet and exit filters 118 and 120 are specified to meet the requirements of the application. For example, the greater the efficiency of the inlet filter 118, the lower the fraction of ambient particles captured by the exit filter 20 that may contribute to a false reading when analyzing for harmful constituent AMCs. Also, the greater the efficiency of the exit filter, the cleaner the flow stream 112 that exits the exit filter 120. Generally, high efficiency filters such as high efficiency particulate air filters (HEPA filters), ultra low particle air filters (ULPA filters) or super ultra low particle air filters (SULPA filters) are adequate for both the inlet and exit filters 118 and 120. HEPA filters remove at least 99.7% of airborne particles, while ULPA and SULPA filters remove 99.999% and 99.9999% of airborne particles, respectively. The filters may be of an all-stainless steel construction to facilitate the high temperatures required to release the captured materials.

Figure 4:
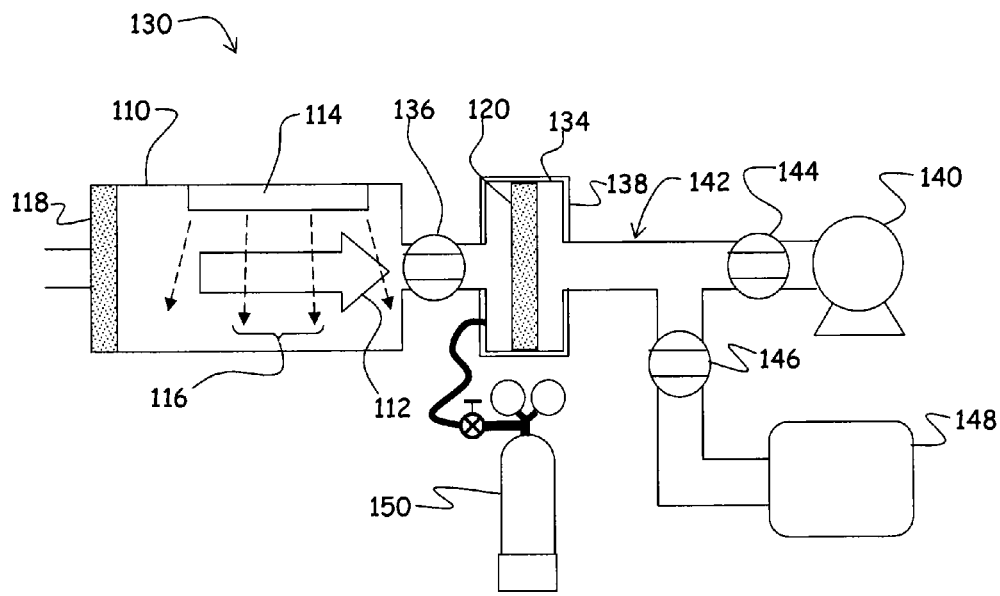
FIG. 4 is a schematic of a conditioning/detecting system for removing harmful AMCs from a flow stream and analyzing the composition of the AMCs in an embodiment of the invention.

Referring to FIG. 4, a conditioning/analysis system 130 for both conditioning and analyzing the constituents of the flow stream 112 is depicted in an embodiment of the invention. The conditioning/analysis system 130 of the depicted embodiment includes the conditioning chamber 110, the ionizing radiation source 114 with attendant ionizing radiation 116, and the inlet and exit filters 118 and 120 of the FIG. 3 embodiment. In addition, the exit filter 120 is contained in a filter chamber 134 that can be isolated from the conditioning chamber 110, for example by an isolation valve 136. In one embodiment, the filter chamber 134 includes a heater 138.

The flow stream 112 may be drawn through the conditioning chamber 110 by a pump 140 located downstream of the filter chamber 134 via a manifold 142. The manifold 142 may be equipped with isolation valves 144 and 146 to enable selective connection to a gas analyzer 148, such as a gas chromatograph or a mass spectrometer. The isolation valves 136 and 144 are depicted in FIG. 4 in the open position for fluid communication with the pump 140. The isolation valve 146 is depicted in the closed position for isolation of the gas analyzer 148. The conditioning/analysis system 130 may further include a carrier gas supply 150 in fluid communication with the upstream side of the exit filter 120.

In operation, the conditioning/analysis system 130 is operated in fluid communication with the pump 140 for an accumulation period of time so that a quantity of radiolytically generated particles collects in the exit filter 120. The volume or mass of the air that flows through the exit filter 120 over the accumulation period may be measured with a flow metering device (not depicted). After the accumulation period is complete, the isolation valves 136 and 140 may be closed and the isolation valve 146 may be opened to place the filter chamber 134 in fluid communication with the gas analyzer 148. The heater 138 may be activated to thermally desorb, thermally decompose and desorb or otherwise "re-gasify" the radiolytically generated particles that are captured in the exit filter 120. The gas that evolves from the re-gasification can then be analyzed by the gas analyzer 148 to identify the composition of the AMCs that caused radiolytic generation of the particles. In one embodiment, the evolved gas is borne on a carrier gas provided by the carrier gas source 150. With or without the use of the carrier gas, the concentration of the AMCs in the evolved gas can be several times greater than the concentration of the flow stream 112 for greater detectability.

The increase in the concentration depends on the accumulation time and flow rate, the time over which the gases are evolved from the heated filter, and the flow rate of any carrier gas that may be used. Different gases may desorb from the filter at different temperatures, so the concentration of the released gases may be variable much like thermal desorption gas chromatography.

Figure 5:
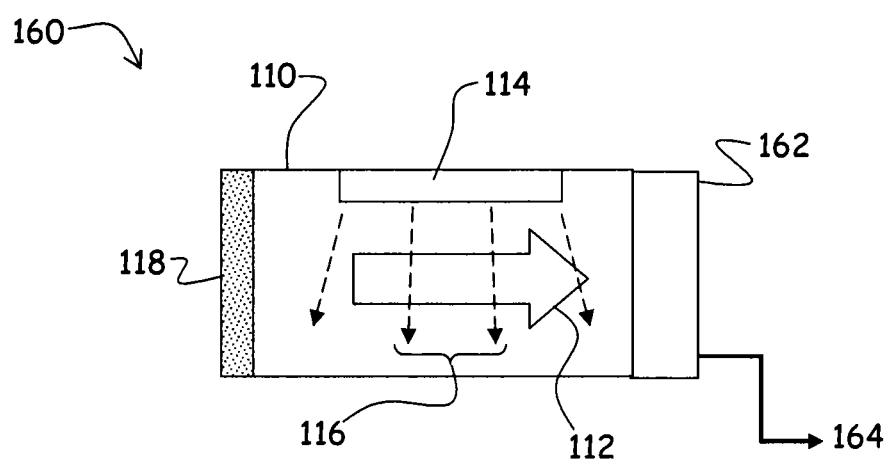
FIG. 5 is a schematic of a detection system for detecting the presence of harmful AMCs in an embodiment of the invention.

Referring to FIG. 5, a detection system 160 for detecting harmful AMCs is depicted in an embodiment of the invention. The detection system 160 as depicted includes the conditioning chamber 110, the ionizing radiation source 114 with attendant ionizing radiation 116, and the inlet filter 118 of the FIGS. 2 and 3 embodiments. A detection system or module 162 is positioned downstream of the ionizing radiation source 114, adapted to generate a signal 164 proportional to the accumulation or accumulation rate of the radiolytic particle generation.

The detection system or module 162 may comprise any device capable of quantifying particles. A condensation particle counter could be used for greatest sensitivity. A charger-electrometer could be utilized for lower cost. An optical particle counter would be suitable if the particles can be grown to large enough sizes. In another embodiment, a photometer could be utilized if particle concentration and size are in the right range.

Functionally, the objective of the detection system 160 is to provide an indication that harmful AMCs are present, and not their removal or subsequent release at higher concentrations for analytical purposes. Accordingly, the detection system 160 can be sized smaller and equipped with lower intensity ionizing radiation source 114 because total removal of harmful AMCs is not an objective of the system.

The foregoing descriptions present numerous specific details that provide a thorough understanding of various embodiments of the present invention. Each of the figures and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention, which is defined solely by the claims that follow.

For purposes of interpreting the claims for the present invention, it is expressly intended that the provisions of Section 112, sixth paragraph of 35 U.S.C. are not to be invoked with respect to a given claim unless the specific terms "means for" or "step for" are recited in that claim.

What is claimed is:

1. A system for detecting airborne molecular contaminants in a gas, comprising:
   a monitored environment configured to received a gas including airborne molecular contaminants, said airborne molecular contaminants including species of interest;
   a substantially monochromatic light source producing a primary beam, said primary beam being split into a reference beam having a reference beam intensity and a test beam having a test beam intensity and wherein an intensity ratio of the test beam intensity to the reference beam intensity is at least 10,000:1;
   a first set of optical components operatively coupled with said monochromatic light source to which the reference beam is routed, said first set of optical components defining a reference beam optical path having a reference optical path length;
   a second set of optical components operatively coupled with said monochromatic light source to which the test beam is routed, said second set of optical components defining a test beam optical path having a test optical path length, said second set of optical components including a test surface exposed to the gas upon which a collection of solid deposits of the species of interest form in response to the test beam at the test surface; and
   detection means for detecting a phase change in said test optical path length as compared to the reference optical path length, said phase change caused by enhanced formation of said collection of solid deposits on the test surface as compared to the reference beam optical path due to the intensity ratio, wherein the detection means senses a rate of said phase change, wherein the rate of said phase change is proportional to a concentration of the species of interest.

2. The system of claim 1 wherein said second set of optical components comprises a fiber optic having a proximal end and a distal end, wherein the proximal end is coupled with said substantially monochromatic light source and wherein the test surface is at the distal end.

3. The system of claim 2 wherein said test beam optical path and said reference beam optical path overlap on said detection means, said detection means comprising a diode array detector.

4. The system of claim 1 wherein said first set of optical components, said second set of optical components and said detection means in combination define a Mach-Zender type interferometer.

5. The system of claim 1 wherein said second set of optical components includes a focusing element and said test surface is an exposed surface of a substrate, said focusing element being configured to focus said test beam on said exposed surface of said substrate.

6. The system of claim 1 wherein said detection means comprises a first detector configured to terminate said reference beam and a second detector configured to terminate said test beam.

7. The system of claim 1 wherein said substantially monochromatic light source is a laser.

8. The system of claim 1 wherein said substantially monochromatic light source emits light at an actinic-wavelength.

9. A system for detecting the presence of airborne molecular contaminants in a gas, comprising:
   a monitored environment configured to receive a gas including airborne molecular contaminants, said airborne molecular contaminants including species of interest;
   a substantially monochromatic light source generating a primary beam;
   a beam splitter splitting the primary beam into a test beam having a test beam intensity and a reference beam having a reference beam intensity and wherein an intensity ratio of the test beam intensity to the reference beam intensity is at least 10,000:1;
   a substrate element having a measuring surface, said measuring surface exposed to the gas;
   a test beam detector; and
   a reference beam detector;
   wherein the test beam is directed through the substrate element such that an emerging test beam exits the substrate element, the test beam being focused on the measuring surface such that a collection of species of interest can form on the measuring surface in response to the test beam at the test surface, and
   wherein growth of the collected species of interest at the measuring surface causes a phase change from the test beam to the emerging test beam as measured by the test beam detector, said emerging test beam being continuously compared in an amplifier to the reference beam measured by the reference beam detector and wherein a measured rate of said phase change as output by the amplifier is proportional to a concentration of the species of interest.

10. A system for detecting the presence of airborne molecular contaminants in a gas, comprising:
    a monitored environment configured to receive a gas including airborne molecular contaminants, said airborne molecular contaminants including species of interest;
    a laser light source for generating a laser light;
    an optical fiber operatively coupled to the laser light source and a coupler, the coupler dividing the laser light into a test fiber optic and a reference fiber optic, the laser light being divided into a test light having a test light intensity and a reference light having a reference light intensity wherein an intensity ratio of test light intensity to reference light intensity is at least 10,000:1, the reference fiber optic having a distal reference fiber optic end that is protected with a transmissive shroud and the test fiber optic including a distal test fiber optic end that is exposed to the gas; and
    an array detector,
    wherein the test light at the distal test fiber optic end of the test fiber optic causes species of interest to form a deposit on the distal test fiber optic end, wherein growth of said deposit at the distal test fiber optic end causes a phase shift in emerging test light from the distal test fiber optic end relative to emerging reference light from the shrouded distal reference fiber optic, wherein an interference pattern is created by overlapping the emerging test light and the emerging reference light; and wherein the phase shift causes the interference pattern to shift, wherein the array detector continually senses a shifting rate of the interference pattern, said shifting rate being proportional to an amount of the species of interest.

* * * * *